United States Patent
Alers et al.

(10) Patent No.: US 7,819,010 B2
(45) Date of Patent: Oct. 26, 2010

(54) DEVICE FOR TESTING FERROMAGNETIC COMPONENT WALLS WITHOUT DESTRUCTION OF THE SAME

(75) Inventors: George A. Alers, San Luis Obispo, CA (US); Ronald B. Alers, San Luis Obispo, CA (US); John J. Boyle, Los Osos, CA (US); Thomas Beuker, Münster (DE)

(73) Assignee: Rosen Swiss AG, Stans (CH)

( * ) Notice: Subject to any disclaimer, the term of this patent is extended or adjusted under 35 U.S.C. 154(b) by 373 days.

(21) Appl. No.: 11/722,568

(22) PCT Filed: Dec. 21, 2005

(86) PCT No.: PCT/EP2005/013747

§ 371 (c)(1), (2), (4) Date: Feb. 6, 2008

(87) PCT Pub. No.: WO2006/069684

PCT Pub. Date: Jul. 6, 2006

(65) Prior Publication Data

US 2009/0078048 A1 Mar. 26, 2009

(30) Foreign Application Priority Data

Dec. 23, 2004 (DE) .................. 10 2004 063 482

(51) Int. Cl.
*G01N 29/04* (2006.01)

(52) U.S. Cl. .................. 73/622; 73/600; 73/624; 73/643

(58) Field of Classification Search ............ 73/622, 73/592, 599, 600, 624, 643
See application file for complete search history.

(56) References Cited

U.S. PATENT DOCUMENTS

| | | | |
|---|---|---|---|
| 4,100,809 A | 7/1978 | Bobrov et al. | |
| 4,301,684 A | 11/1981 | Thompson et al. | |
| 4,466,287 A | 8/1984 | Repplinger et al. | |
| 5,537,876 A | 7/1996 | Davidson et al. | |
| 5,721,379 A * | 2/1998 | Palmer et al. | 73/643 |
| 5,866,820 A | 2/1999 | Camplin et al. | |
| 6,109,108 A * | 8/2000 | Ohtani et al. | 73/599 |
| 6,125,703 A * | 10/2000 | MacLauchlan et al. | 73/592 |
| 6,250,163 B1 | 6/2001 | MacLauchlan et al. | |

(Continued)

FOREIGN PATENT DOCUMENTS

EP 0867718 A2 9/1998

*Primary Examiner*—J M Saint Surin
(74) *Attorney, Agent, or Firm*—Gudrun E. Huckett (57) ABSTRACT

A device for destruction-free testing of ferromagnetic component walls with respect to elongate defects has a sending transducer that excites ultrasound waves in a wall area of a ferromagnetic component wall magnetized in a predetermined direction of magnetization. The ultrasound waves propagate on a path oriented by the sending transducer. A receiving transducer receives the ultrasound waves at a spacing from the sending transducer. The configuration of the sending transducer and a high frequency emitted by the sending transducer, which high frequency is to be determined based on a thickness of the ferromagnetic component wall, are selected so as to effect excitation of horizontal shear waves of higher order. The path orientation is selected at a slant angle to the predetermined direction of magnetization. The receiving transducer is positioned lateral to the path and is oriented toward a predetermined testing area of the wall section in the path.

21 Claims, 4 Drawing Sheets

U.S. PATENT DOCUMENTS

| | | | |
|---|---|---|---|
| 6,373,245 B1 * | 4/2002 | Kwun et al. | 324/240 |
| 6,502,463 B1 * | 1/2003 | Clark et al. | 73/643 |
| 6,561,035 B2 * | 5/2003 | Passarelli, Jr. | 73/643 |
| 6,896,171 B2 * | 5/2005 | Den Boer et al. | 228/103 |
| 7,406,873 B2 * | 8/2008 | Paige et al. | 73/643 |
| 7,546,770 B2 * | 6/2009 | Meethal et al. | 73/643 |

* cited by examiner

DEVICE FOR TESTING FERROMAGNETIC COMPONENT WALLS WITHOUT DESTRUCTION OF THE SAME

BACKGROUND OF THE INVENTION

The invention relates to a device for destruction-free testing of ferromagnetic component walls such as pipe walls or panel walls with respect to cracks or other elongate defects by ultrasound waves, in particular shear waves, that are excited by a high frequency induction coil in a wall area magnetized in a predetermined direction, that propagate on a path that can be oriented by the induction coil as a sending transducer and that are received at a spacing from the sending transducer by at least one induction coil as a receiving transducer. On different components, in particular, in the exterior area, tests in regard to possible defects are mandatory at predetermined time intervals in order to counteract the risk of failure in the sense of breakage, deformation, or leakage. Walls of pipes as well as walls of containers or the like made from steel are often corrosion-prone. In particular, they can be exposed to stress crack corrosion with typical cracks or crack bundles that penetrate, starting at the surface, into the depth. Likewise, cracks as a result of other causes such as, in particular, overloads are to be considered. In addition, other defects such as corrosion locations are of interest.

Destruction-free testing methods employ, for example, ultrasound methods wherein the excitation of acoustic waves in the wall can be realized from the exterior by means of electromagnetic-acoustic transducers. This so-called EMAT (electromagnetic-acoustic transducer) enables the contact-less excitation of acoustic lamb waves, in particular, without coupling medium, in such a wall. In this connection, the excitation of "lamb waves", as well as of shear waves, that are polarized parallel to the wall surface is much easier and more flexible than by mechanical generation by means of piezo transducers. Such shear waves propagate transverse to the polarization or to the excitation deflection relatively bundled in two opposite directions. These shear waves that must be excited by a suitable frequency for generating a useable excitation with a high frequency induction coil that is geometrically matched particularly with regard to conductor spacings, wherein suitable frequency ranges and conductor spacings vary also with the thickness of the wall, can generate different wave shapes as a function of the depth within the wall. For example, a shear wave of zero order oscillates in the interior of the wall and also at the opposite surface uniformly with the top wall surface while a shear wave of first order forms a node at the center of the wall and at the opposite surface oscillates in the opposite direction. Shear waves of higher order form several nodes within the wall. These wave shapes are suitable in different ways for the detection of defects. Moreover, the oscillation excitation as well as its detection by means of sending or receiving transducers must be detectable as clearly and disruption-free as possible.

SUMMARY OF THE INVENTION

Object of the invention is therefore to configure a device for a destruction-free testing of ferromagnetic components according to the aforementioned kind in such a way that these defects of a predetermined shape, in particular, also cracks or crack bundles, for example, based on stress crack corrosion that penetrate from the surface into the wall and generally has a typical orientation, can be detected well without this requiring increasing the construction expenditure and the energy expenditure of the device inappropriately.

According to the invention, this object is solved for the device of the aforementioned kind in that the configuration of the transducer and the high frequency to be determined based on the thickness of the wall are selected for effecting the excitation of horizontal shear waves of higher order, in that the orientation of the path is at a slant angle $\alpha$ relative to the magnet orientation (B), and in that the receiving transducer is positioned lateral to the path and is oriented toward a predetermined testing area in the path.

In a further development of the already known technology of destruction-free testing of ferromagnetic components with electromagnetically induced ultrasound shear waves, it has been found to be advantageous for special applications, in particular, for searching cracks that penetrate only across a portion of the thickness into the wall, to excite shear waves of higher order and to enhance in particular the surface-near area and to accentuate its detection in this way. Already a shear wave of first order is capable of suppressing measuring-technologically with inwardly decreasing wave amplitudes a central inwardly positioned area of the wall during testing. This holds true even more for a shear wave of second order. Shear waves of higher order exhibit greater sensitivity with regard to surface-near defects, wherein however the mode dispersion increases with increasing order leading to diverging wave packages. The shear wave of second order is an often particularly fortunate combination between the selection of the testing depth of interest within the wall, a reliable and controllable function of the sending transducer, and a satisfactory signal in a correlated receiving transducer.

For the electromagnetic induction of ultrasound waves a magnetization of the area to be tested of the component wall is to be provided; usually, this can be achieved by one or several permanent magnets wherein a magnetic circuit, optionally with a magnet yoke, is closed through the wall of the component to be tested. In this context it can be observed that an orientation of the path of the induced waves in accordance with the magnet orientation triggers a plurality of oscillation components, lamb waves included, as a result of the occurring Lorentz forces, but the horizontal polarized shear waves of higher order that are of particular interest in the present case and are obtainable by magnetostrictive effects can be generated and received particular beneficially when the orientation of the path is at a slant angle to the magnet orientation. This angle between the orientation of the path and the magnet orientation should be advantageously between 10 degrees and 60 degrees, optimally between 20 degrees and 50 degrees.

Advantageously, a receiving transducer is positioned lateral to the path and oriented toward a predetermined testing area in the path so that, on the one hand, it receives scattered or reflected signals from this testing area easily but receives the signals directly emitted from the sending transducer only to a reduced degree; these direct signals, as a result of the orientation toward the testing area (and not toward the sending transducer), are therefore detected at a reduced level already because of the receiving characteristics.

The orientation of the receiving transducer onto a predetermined testing area in the path that follows itself the orientation of the sending transducer results only in an angular orientation of sending transducer and receiving transducer relative to one another. In the case of cracks or similar elongate defects such as stress cracks or stress crack bundles, a diffuse scattering of the occurring shear waves is not to be expected but, instead, a wave reflection with approximately mirror-symmetrical conditions between impinging and reflected waves wherein the receiving transducer is to be oriented toward the resulting reflection angle for a known orientation or a primarily important orientation of the defects.

With regard to these angle conditions it should be noted that the magnet orientation is not fixed to the main direction of the defects. The magnetization of the component wall as the basis of the induction effects of sending transducer and receiving transducer can be predetermined, of course, so as to deviate from the assumed main direction of the defects. The requirement that the orientation of the path of the shear wave should be positioned at a slant angle to the magnet orientation and that the sending transducer and receiving transducer should cooperate with regard to reflections of the defects, can lead however to an advantageous and simple determination that the magnet orientation follows the main direction of the defects or is perpendicular to this main direction.

The geometric conditions are not only to be taken into consideration for an effective excitation of shear waves and a sensitive and reliable testing of ferromagnetic walls with regard to defects, they also are taken into account in the construction of such devices. For an efficient testing of large surface area walls, for example, of containers, movable measuring devices with a plurality of such devices, tightly spaced, are provided for a destruction-free testing; they scan the wall with their testing areas in strip-shaped passes without leaving any gaps. Even more important is the field of application in regard to pipelines whose entire wall circumference is to be tested without destruction by passing a measuring pig therethrough. In this case there is also a working width for the measuring pig that is determined by the wall circumference which working width can be realized only with a plurality of adjoining devices of the kind considered herein.

BRIEF DESCRIPTION OF THE DRAWINGS

Embodiments of the article of the invention result from the drawing and the following description. The drawings show in.

DESCRIPTION OF PREFERRED EMBODIMENTS

Figure 1:
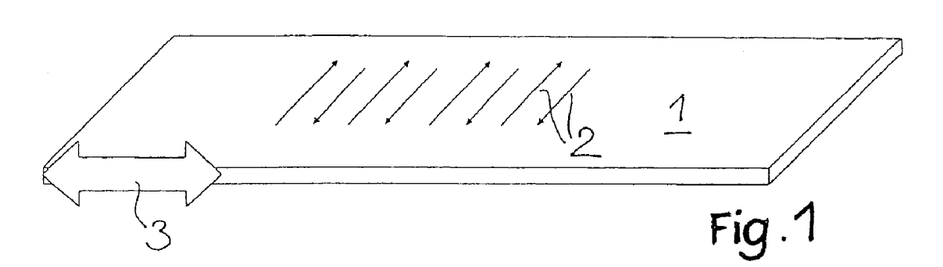
FIG. 1 a perspective view of a panel wall with directional arrows for the deflection at the surface in the case of a shear wave.

FIG. 1 shows a wall panel (or a corresponding wall section) referenced by 1 on which the alternating directional arrows 2 indicate the oscillations of the material as a result of a standing or fading shear wave at a certain time of observation. Such a shear wave can be induced contactless in the panel 1 approximately at the level of the double arrow 3 by an electromagnetic-acoustic transducer (EMAT); the arrow indicates also a propagation with beginning excitation in both directions of the double arrow 3.

Figure 2:
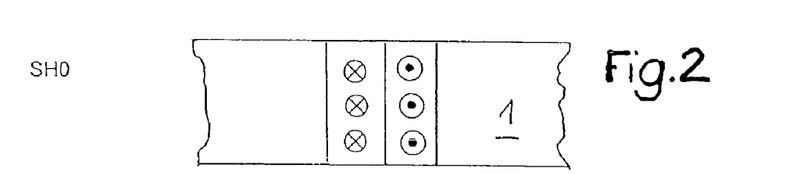
FIGS. 2, 3, and 4 a longitudinal section of a panel for shear waves of zero, first or second order.
Figure 3:
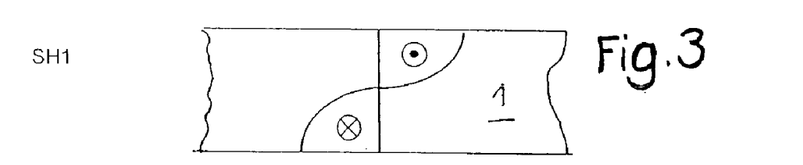
Figure 4:
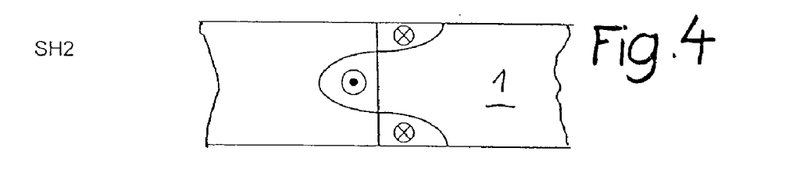

FIGS. 2, 3, and 4 illustrates that the shear waves must not at all propagate uniformly to the interior of the panel. This is the case only for a shear wave of zero order SH0 according to FIG. 2. A shear wave of first order SH1 according to FIG. 3 oscillates instead at a panel surface in opposite direction to the other surface and generates nodes at the panel center. Already for this reason, a reduced participation in the oscillation of the material in the interior of the panel relative to the panel surface will result.

The horizontal shear wave of second order SH2 with two nodes is even more limited to the surface-near participation in the shear wave, in particular, because the oscillations at the surface are relevant for the receiving signals that can be received inductively from the exterior. This is of particular interest for cracks or similar defects that penetrate from the exterior, for example, as the result of stress crack corrosion, into a panel or wall. Defects with limited penetration depth are of particular interest in the case of inspection and are detected much better by horizontal shear waves of higher order than by a shear wave of zero order. The term "shear waves of higher order" refers thus in this context to shear waves of greater than zero order (SH0).

Figure 5:
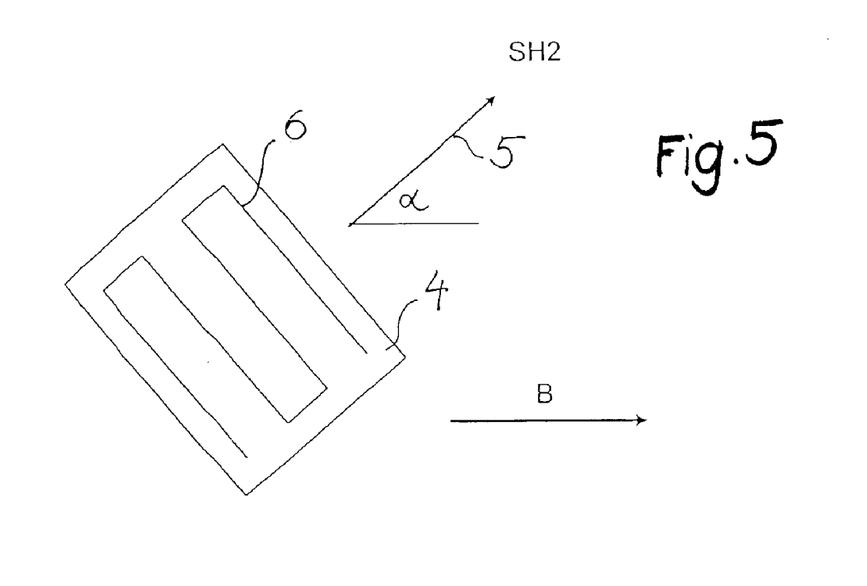
FIGS. 5 to 11 schematic illustrations of sending transducers in relation to the magnet orientation.

For exciting such shear waves, generally a magnetization of the ferromagnetic wall is a prerequisite; it is in general realized as a static magnetization by means of a permanent magnet circuit, wherein the magnetic flux of one for several strong permanent magnets, optionally also by means of magnet yokes and pole shoes, is introduced at two spaced-apart locations into the wall and is passed through the wall. This is indicated in FIG. 5 with arrow B for the magnetic induction indicating a uniform magnetization with identical orientation in a panel above which a sending transducer 4 is arranged that is supposed to excite a shear wave of second order SH2 that propagates in the direction of arrow 5 (and in the opposite direction).

An efficient excitation requires a suitable geometric shape of a generally meander-shaped induction coil 6 with optimized spacing between the conductors and, moreover, a matching induction signal in particular with regard to the frequency, wherein the frequency is a high frequency that can be approximately within the range of 10 kHz to 5 MHz and is determined concretely in accordance with the order of the shear wave to be excited and the thickness of the wall.

Moreover, it was found that the emission direction of the shear wave in accordance with arrow 5 is important in particular for the effectivity of the excitation but also for the suppression of other waves that are disruptive during testing. A slant angle α, as indicated between arrow 5 and the arrow B, has advantages indeed. While emission of the sending transducer 4 in the magnet orientation according to arrow B generates a high proportion of other, in particular, lamb waves, a maximum for the emission of horizontal shear waves SH2 results at a slant angle range of 20 degrees to 50 degrees and a somewhat reduced but still advantageous emission at a further slant angle range between 10 degrees and 60 degrees.

Figure 6:
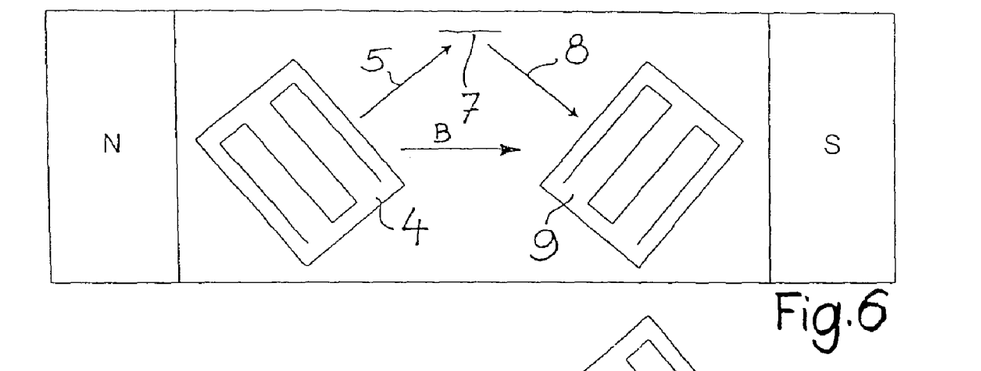

FIG. 6 shows more completely that the magnet orientation with arrow B extends through a static magnetic field between a magnetic north pole N and a magnetic south pole S and that the sending transducer 4 emits horizontal shear waves in the direction of arrow 5. They impinge in the illustrated situation on a crack 7 beginning at the surface and extending substantially straight but only with a penetration depth that is limited to a fraction of the wall thickness of the component wall to be tested. As a shear wave of higher order with corresponding primary detection of the surface-near area of the wall to be tested, this shear wave is subjected to a significant reflection in the direction of arrow 8. The reflected wave is received by a receiving transducer 9, that can be designed in principle in analogy to the sending transducer 4, and is further conducted to suitable measuring and recording device. This means that signals are received that describe the crack based on the received signals in the receiving transducer 9. The receiving transducer 9 is oriented perpendicularly to the arrow 8 for the reflection direction of the shear wave wherein the propagation directions according to FIGS. 5 and 8 in accordance with the general rules for the reflection of waves are mirror-symmetrical to the normal onto the main orientation of the crack 7.

The crack 7 is assumed to be approximately parallel to the magnet orientation in accordance with arrow B so that the reflected wave according to arrow 8 extends at a corresponding slant angle α relative to the magnetization according to arrow B. Accordingly, beneficial physical receiving conditions results also for the receiving transducer 9.

Figure 7:
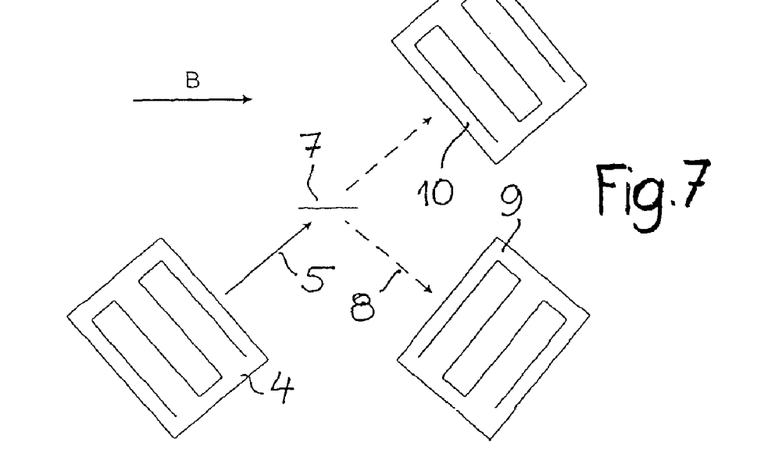

FIG. 7 shows an arrangement, in which the static magnetization is indicated only by arrow B, supplemented by a further receiving transducer, i.e., a reference transducer 10 that is embodied in analogy to the receiving transducer 9 but is positioned and aligned opposite the sending transducer 4 in the direction of arrow 5, but at the same propagation distance as the sending transducer 9, so that it receives entirely or partially passing shear waves. The resulting signal provides thus a reference signal for the receiving transducer 9 with which the receiving signal, when no reflection occurs, i.e., within a wall area without defects, can be standardized and with which, when a reflection signal occurs in the receiving transducer 9, a conclusion with regard to the strength of the reflection signals can be derived. This provides a reference parameter for the geometric evaluation of the detected defect independent of the optionally material-dependent but also fluctuating quality of the coupling of the shear waves by means of the sending transducer 4 and the receiving efficiency of the receiving transducer 9.

Figure 8:
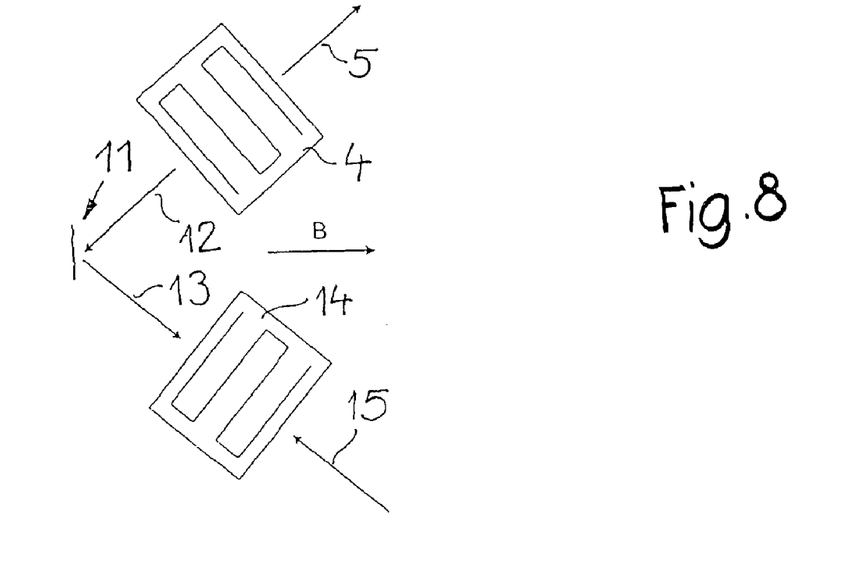

In FIG. 8, a supplement of the preceding measuring arrangement of FIG. 7 is illustrated which, however, can also be used alone as an alternative for testing transversely extending cracks. This concerns defects that extend transversely to the magnetization direction (induction arrow B). Such a crack 11 can be detected with the second propagation direction of the induced shear wave opposite to the arrow 5 in the direction of arrow 12 in order to achieve thus a reflection in the direction of arrow 13. This reflection can be received by a receiving transducer 14 in a suitable position and in orientation toward the reflection in the direction of arrow 13. This also provides a beneficial receiving angle α relative to the magnetization.

In cooperation with several sending transducers, the receiving transducer 14 (and accordingly also any other receiving transducer) can receive shear waves that come in from opposite directions, as indicated by arrow 15. In this way, configurations are taking into account which, in a compact arrangement, have a plurality of sending transducers and receiving transducers that scan in a broad, closed array a strip on a plane wall or a pipe cross-section in one pass.

Moreover, FIGS. 7 and 8 show that with the orientation and positioning of the transducers relative to one another cracks can be detected that extend in the direction of the magnetic field as well as those that extend primarily transversely. In this way, when, for example, longitudinal cracks are to be detected in a pipe, a magnetization in the transverse direction (circumferential direction) can be used also; this then enables, naturally with a different correlation of transducers, the detection of longitudinal cracks.

Figure 9:
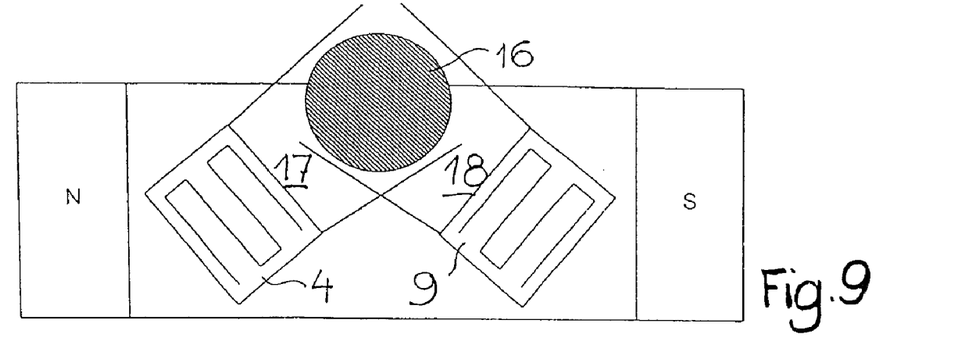
Figure 10:
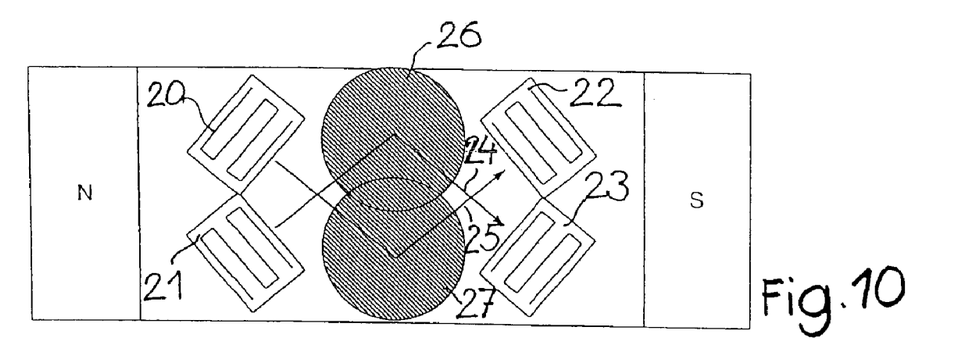
Figure 11:
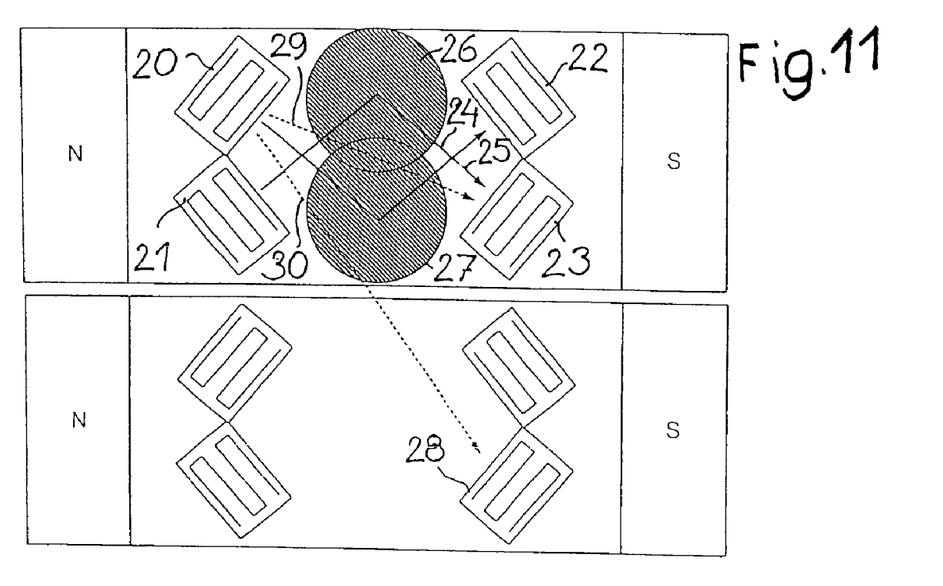

FIGS. 9 through 11 show that the gap-free detection of a ferromagnetic component wall, in particular, a pipe wall, can be realized by a combination of the devices according to the invention. In FIG. 9, the measuring arrangement discussed in connection with FIG. 6 is illustrated in which a homogenous magnetic field between a north pole N and a south pole S is provided in a component wall, and between these magnetic poles in the area of the magnetic field, a sending transducer 4 and a receiving transducer 9 are arranged. Both are oriented toward a testing area 16 in which possibly present defects are to be detected. For this purpose, shear waves induced by the sending transducer 4 are emitted in a (utilized) direction wherein a predetermined useable wave energy is detected in the area of a path 17 that extends with pronounced bundling, even though with a certain broadening, from the sending transducer 4 to the testing area 16 and past it.

Likewise, for the sending transducer 9 on the side of the testing area 16 a directed and reasonably bundled area—illustrated here only by area 18—can be recognized from which the impinging shear waves are received sufficiently clearly, optionally as a reflection. The directional characteristics of both EMAT transducers is thus characterized by a bundling referred to as "path". In this connection, it is of interest to select the travel distance of the acoustic waves to be as short as possible in order to minimize geometric propagation losses.

In a configuration according to FIG. 10 within the static magnetic field between the illustrated north pole N and south pole S two sending transducers 20, 21 and two receiving transducers 22, 23 are arranged such that they cooperate in pairs on predetermined crossing reflection lines 24, 25, namely relative to two testing areas 26, 27 that supplement one another with minimal overlap such that the entire width of the magnetic poles is covered. A movement of the corresponding device in the direction of the magnetic field thus leads to covering the entire width of the testing areas 26, 27. The magnetization provided by the magnetic poles is used for the two testing devices that operate in a crossed arrangement relative to one another.

The arrangement illustrated in FIG. 11 of several such permanent magnets with corresponding testing pairs according to FIG. 10 however shows also that crosstalk between receiving transducers and sending transducers that are not correlated with on another with regard to reflection can take place which. This is however indeed informative in regard to measuring technological aspects when, for example, signals emitted by the sending transducer 20 are received by the receiving transducer 23 that is actually oriented to receive reflection waves that are emitted by the sending transducer 21. Also, signals of the sending transducer 20 passing a receiving transducer 28 can be received. Such receiving signals whose paths are indicated by arrows 29, 30 in dashed lines are to be evaluated in accordance with transient time and damping. In particular, damping in the case of coated or covered panels or pipes provides information in regard to the state of the coating or covering. A missing coating or a coating that has become detached from the surface of the ferromagnetic wall as a result of corrosion or corrosion creep causes a significantly reduced damping of the shear wave relative to its travel distance and indicates thus a faulty coating.

The electromagnetic acoustic excitation of shear waves is based on sending transducers that have a known shape as illustrated in FIGS. 5 to 11, i.e, they are comprised of a sequence of meanders. The shape is to be matched to the desired shear waves. In this connection, the parallel long conductor sections of the meanders define a main direction that is also the propagation direction of the shear waves. Various embodiments of the corresponding induction coils are illustrated in FIGS. 12 through 17. Moreover, it is important to provide an excellent space utilization within the magnetic field with short paths for the sound waves and their reflections.

Figures 12, 13:
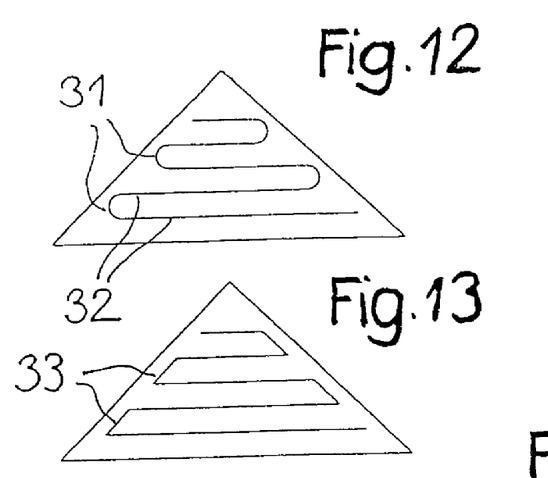
FIGS. 12 to 17 embodiments of induction coils for the EMAT transducers.
Figure 14:
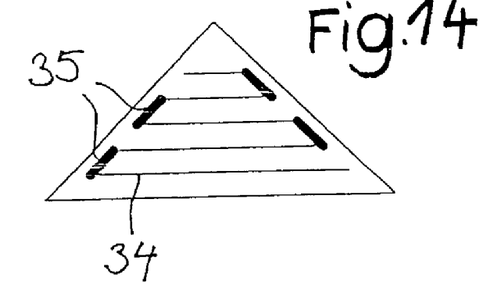

The embodiments of induction coils illustrated in FIGS. 12 to 14 are to be arranged on a surface in the form of a right triangle. This makes it possible to arrange the sending transducer and receiving transducer in a space-saving way in corner areas of the space that is available between the north pole and the south pole, for example, in accordance with FIG. 6, and to determine at an actually beneficial slant of approximately 45 degrees to the magnet orientation a path for the shear wave propagation and also for its reflections. Rounded deflections 31 on the conductors 32 as shown in FIG. 12 avoid secondary emission in any other direction while straight deflection sections 33 as in FIG. 13 cause secondary emission in the transverse direction to these conductor sections 33 that can optionally be used for auxiliary measurements. For example, ultrasound lamb waves can be induced with a testing pass of a pig through a pipe in the longitudinal direction of the pipe; the reflections indicate primarily welding seams in the pipe for a position determination.

The conductor loop 34 according to FIG. 14 with broadened loops 35 provides reduced current densities at the broadened sections that cause reduced electromechanical excitation forces and thus also suppress secondary emissions in the same way as the rounded loops 31.

Figure 15:
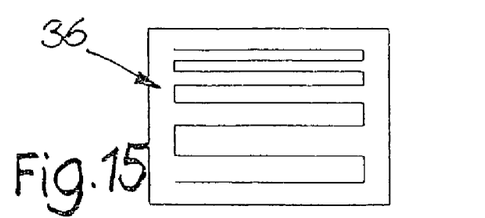
Figure 16:
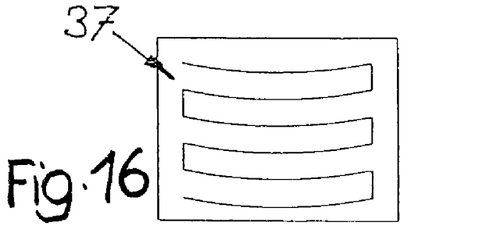
Figure 17:
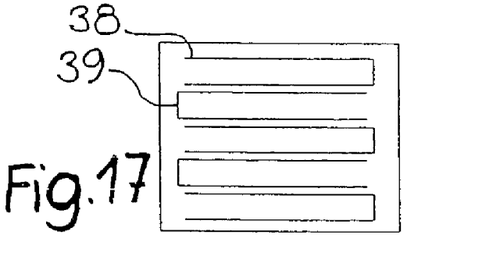

FIGS. 15 to 17 show loop-shaped EMAT coils in a generally rectangular arrangement. In a configuration of a coil geometry 36 according to FIG. 15 a pulse compression can be achieved in that the conductor spacings and thus the wave length are varied monotonously ("chirping") because the speed of the shear waves of higher order is a function of the wavelength. For a sufficient bandwidth of excitation a wave package can be generated that as a result of dispersion will converge and in this way cause the amplitude to increase. This is useful in particular in the pulse echo method for determining the echo transient time as a measure for the distance of a reflected defect relative to the sending and receiving transducers.

A curvature of the conductors 36 in the shape of a concave mirror in an induction coil according to FIG. 16 leads to a reduction of the opening angle of the sound bundle. In this way, the testing area is made smaller and the localization is made more precise when the upward propagation direction is considered in accordance with FIG. 16. In the opposite propagation direction defocussing occurs that enables widening of the testing area.

An induction coil according to FIG. 17 is comprised of a plurality of individual conductor loops 38, 39 that are controlled individually at a spacing to one another that is to be determined. By phase displacement between the individual excitations a control of the emission characteristics is possible ("phased array") while an amplitude modulation can be utilized for optimizing the signal shape of the acoustic wave ("apodization", "shading").

Such induction coils are excited, for example, at a frequency of 500 kilohertz at a sequence of 15 pulses, according to which ultrasound waves, in particular also the shear waves of higher order referred to herein, are excited in the material to be tested. Short pulse sequences in this frequency range enable operation at cycle frequencies of a few hundred hertz without this causing crosstalk in the case of interaction of many testing devices that are spatially neighboring one another. In this way, even for measuring devices as, for example, measuring pigs in pipes having a travel speed of several meters per second, measuring repetitions are possible in such a tight sequence that no inspection gaps will occur even in the movement direction of such a measuring pig.

The invention claimed is:

1. A device for destruction-free testing of ferromagnetic component walls with respect to elongate defects, said device comprising:
at least one sending transducer in the form of a high frequency induction coil which at least one sending transducer excites ultrasound waves in a wall area of a ferromagnetic component wall that is magnetized in a predetermined direction of magnetization, wherein the ultrasound waves propagate on a path that is oriented by the at least one sending transducer;
at least one receiving transducer in the form of an induction coil, wherein the at least one sending transducer receives the ultrasound waves at a spacing from the at least one sending transducer;
wherein a configuration of the at least one sending transducer and a high frequency emitted by the at least one sending transducer, which high frequency is to be determined based on a thickness of said ferromagnetic component wall, are selected so as to effect excitation of horizontal shear waves of higher order;
wherein an orientation of said path is selected at a slant angle relative to said predetermined direction of magnetization;
wherein the at least one receiving transducer is positioned lateral to said path and is oriented toward a predetermined testing area of said wall section of said ferromagnetic component wall in said path.

2. The device according to claim 1, wherein said slant angle is between 20 degrees and 60 degrees.

3. The device according to claim 1, wherein said slant angle is in the range of 30 degrees to 50 degrees.

4. The device according to claim 1, wherein the at least one sending transducer and the at least one receiving transducer are oriented relative to a main direction determined for elongate defects in accordance with impinging angle and reflection angle.

5. The device according to claim 4, wherein said wall section is part of a pipe and is magnetized parallel to an axis of the pipe, wherein the at least one sending transducer and the at least one receiving transducer are positioned relative to one another at opposite but identical angles relative to the axis of the pipe.

6. The device according to claim 4, wherein said wall section is part of a pipe and is magnetized in a circumferential direction of the pipe, wherein the at least one sending transducer and the at least one receiving transducer are positioned relative to one another at opposite but identical angles relative to the circumferential direction.

7. The device according to claim 1, further comprising a reference transducer positioned in said path behind the testing area and oriented toward the at least one sending transducer.

8. The device according to claim 1, wherein said path is utilized on opposite sides of the at least one sending transducer for testing defects and wherein a second one of said at least one receiving transducer is positioned lateral to said path and is oriented toward a second testing area of said wall section.

9. The device according to claim 1, wherein the at least one sending transducer generates a secondary emission by means of conductor sections that extend in the same direction.

10. The device according to claim 1, wherein the at least one sending transducer and the at least one receiving transducer are provided in pairs, respectively, and have oppositely oriented crossed paths providing testing areas that adjoin one another without gap.

11. The device according to claim 1, wherein the at least one sending transducer and the at least one receiving transducer are combined for measuring transient time and damping.

12. The device according to claim 1, connected to devices of the same type to form a system with testing areas that supplement one another free of gaps.

13. The device according to claim 12, arranged on the periphery of a measuring pig for a destruction-free testing of pipe walls.

14. The device according to claim 1, wherein the induction coil of the at least one sending transducer or of the at least one receiving transducer has a triangular base surface.

15. The device according to claim 14, wherein the induction soil has conductors positioned in the form of meanders and comprising several long parallel conductor sections.

16. The device according to claim 15, wherein the long parallel conductor sections are connected to one another by arcs.

17. The device according to claim 15, wherein the long parallel conductor sections are connected to one another by short conductor sections, wherein the short conductor sections have identical orientation relative to one another.

18. The device according to claim 15, wherein the long parallel conductor sections are connected to one another by broadened conductor sections.

19. The device according to claim 15, wherein the long parallel conductor sections have different spacings which spacings are varied sequentially monotonously.

20. The device according to claim 15, wherein the long parallel conductor sections are bent in the same direction.

21. The device according to claim 15, wherein the long parallel conductor sections have several separately controlled conductor loops.

* * * * *

UNITED STATES PATENT AND TRADEMARK OFFICE
CERTIFICATE OF CORRECTION

Page 1 of 1

PATENT NO.         : 7,819,010 B2
APPLICATION NO.    : 11/722568
DATED              : October 26, 2010
INVENTOR(S)        : George Alers et al.

It is certified that error appears in the above-identified patent and that said Letters Patent is hereby corrected as shown below:

In claim 1 (column 8, line 7), change "wherein the at least one sending transducer receives" to --wherein the at least one receiving transducer receives--.

Signed and Sealed this
Twenty-seventh Day of September, 2011

David J. Kappos
*Director of the United States Patent and Trademark Office*